United States Patent
Zhang

(10) Patent No.: US 10,766,833 B2
(45) Date of Patent: Sep. 8, 2020

(54) HYDROFORMYLATION METHOD AND CATALYST USING RHODIUM-RUTHENIUM DUAL METAL AND TETRADENTATE PHOSPHINE LIGAND

(71) Applicant: WUHAN CATALYS TECHNOLOGY CO., LTD, Wuhan (CN)

(72) Inventor: Xumu Zhang, Wuhan (CN)

(73) Assignee: Wuhan Catalys Technology CO., LTD, Wuhan (CN)

( * ) Notice: Subject to any disclaimer, the term of this patent is extended or adjusted under 35 U.S.C. 154(b) by 0 days.

(21) Appl. No.: 16/509,530

(22) Filed: Jul. 12, 2019

(65) Prior Publication Data

US 2019/0337866 A1     Nov. 7, 2019

Related U.S. Application Data

(63) Continuation of application No. PCT/CN2017/112536, filed on Nov. 23, 2017.

(30) Foreign Application Priority Data

Jan. 12, 2017  (CN) .......................... 2017 1 0023345

(51) Int. Cl.
| | | |
|---|---|---|
| *C07C 45/50* | (2006.01) | |
| *C07B 41/06* | (2006.01) | |
| *B01J 31/00* | (2006.01) | |
| *B01J 31/18* | (2006.01) | |
| *B01J 31/20* | (2006.01) | |
| *B01J 31/24* | (2006.01) | |
| *C07F 9/52* | (2006.01) | |

(52) U.S. Cl.
CPC .............. *C07B 41/06* (2013.01); *B01J 31/181* (2013.01); *B01J 31/20* (2013.01); *B01J 31/2409* (2013.01); *C07F 9/52* (2013.01); *B01J 2231/321* (2013.01); *B01J 2531/821* (2013.01); *B01J 2531/822* (2013.01)

(58) Field of Classification Search
CPC ........ C07C 45/50; C07B 41/06; B01J 31/181; B01J 31/20; B01J 31/2409
See application file for complete search history.

(56) References Cited

FOREIGN PATENT DOCUMENTS

| CN | 1610688 A | 4/2015 |
| CN | 101331144 A | 12/2018 |

OTHER PUBLICATIONS

Yuki et al. Tandem Isomerization/Hydroformylation/Hydrogenation of Internal Alkenes to n-Alcohols using Rh/Ru Dual or Ternary-Catalyst Systems. Journal of the American Chemical Society, vol. 135, 17393-17400. (Year: 2013).*
Vilches-Herrera et al. Isomerization-Hydroformylation Tandem Reactions. ACS Catalysis, vol. 4, 1706-1724. (Year: 2014).*
Beller et al. Dual Catalytic Systems for Consecutive Isomerization-Hydroformylation Reactions. Chem. Eur. J., vol. 5 (4), 1301-1305. (Year: 1999).*
Ksenia Kartashova, Sonia Mallet-Ladeira, M. Rosa Axet, "Synthesis of a bimetallic PeN bridged rhodium(I)eruthenium (II) complex: Application in the hydroformylation reaction". Journal of Organometallic Chemistry, Oct. 22, 2015.

* cited by examiner

*Primary Examiner* — Sikarl A Witherspoon
(74) *Attorney, Agent, or Firm* — Wayne & Ken, LLC; Tony Hom

(57) ABSTRACT

A homogeneous catalytic reaction method and a catalyst for isomerization and hydroformylation of long-chain internal olefins are disclosed. A rhodium-ruthenium metal complex is used as a catalyst; and the ligands are tetradentate phosphine ligands. By means of the catalytic system, homogeneous internal olefin isomerization aid hydroformylation can be performed under a certain temperature and pressure to obtain aldehyde products having high normal to iso ratios. The present invention is applicable to not only long-chain internal olefins (≥C8) but also internal olefins having a carbon number less than 8.

8 Claims, No Drawings

HYDROFORMYLATION METHOD AND CATALYST USING RHODIUM-RUTHENIUM DUAL METAL AND TETRADENTATE PHOSPHINE LIGAND

TECHNICAL FIELD

The invention relates to a method and a catalyst for isomerization and hydroformylation of internal olefins, in particular to a catalytic system with a rhodium-ruthenium dual metal complex combined with a biphenyl tetraphosphine ligand, and a method tor isomerization and hydroformylation of long chain internal olefins for a homogeneous reaction system.

BACKGROUND

The hydroformylation technique, also known as the "Oxo synthesis", has been one of the largest homogeneous reactions in the industrial sector since it was discovered by Often Roelen in 1938 (*Chem. Abstr.* 1944, 3631). Each year, various aldehydes and alcohols produced from Fe, Zn, Mn, Co, Cu, Ag, Ni, Pt, Pd, Rh, Ru and Ir based catalysts have been over 10 million tons. In these catalytic reactions, the ability to achieve high selectivity of linear products (i.e. high linear (normal) to branch (normal) ratio, or l/b) is extremely important for industrial applications. Although large-scale chemical companies and research institutes such as BASF, Dow, Shell, Eastman, LIKAT (Leibniz Institute for Catalysis) and etc. have reported and patented such catalytic reactions in a large amount, linear selectivity is still a practical problem to be solved. New theories and methods for controlling linear selectivity are crucial for hydroformylation reactions. In particular, catalysts with high linear selectivity can produce chemicals in a more environmentally friendly manner under mild conditions.

In industrial hydroformylation reactions, cobalt catalysts (e.g. $HCo(CO)_4$) are in a dominant position until the advent of rhodium catalyst (e.g., $HRh(CO)_2(PPh_3)_3$) in the 1970s. In 2004, it was estimated that approximately 75% of the hydroformylation reactions worldwide were based on a rhodium-triarylphosphine catalyst system. The efficient selectivity of linear aldehyde products is critical in hydroformylation and its related reactions. The aldehyde product is also an important intermediate in addition to chemicals such as perfumes. The further obtained aldehydes can be further hydrogenated, oxidized and animated to be converted into alcohols, carboxylic acids and amines, and used in bulk chemicals, plasticizers, detergents, surfactants, various solvents, lubricants, coatings and other optical materials, etc.

The $HRh(CO)(PPh_3)_2$ catalytic system (*J. Org. Chem.*, 1969, 34, 327-330) invented by Pruett and Smith at Union Carbide coordinates rhodium with an excess amount of phosphine ligands, to form an active and selective hydroformylation species and successfully commercialized. The $HRh(CO)(PPh_3)_2$ catalytic system requires a large amount of phosphine ligand because the Rh-$PPh_3$ complex is easily decomposed in the catalytic system, and triphenylphosphine ($PPh_3$) lost from $HRh(CO)(PPh_3)_2$ will turn the complex into more active but less selective complexes: $HRh(CO)_2(PPh_3)$ and $HRh(CO)_3$. Therefore, taking 1-hexene as an example, in industrial process, it is necessary to use up to 820 times excess of $PPh_3$ to Rh to ensure higher selectivity of linear to branched aldehyde products, wherein the selectivity is up to 17:1. In addition, the industrial reaction of propylene uses a 400 times excess of $PPh_3$ to Rh, and the ratio of linear to branched aldehyde products is 8 to 9:1.

In the hydroformylation process, it is important to use less expensive starting materials as reactants. For example, 2-octene and 3-octene are ideal starting materials for the conversion of long-chain internal olefins to linear aldehydes. Raffinate II (a mixture of butenes and butane) or a mixture of 1-butene and 2-butenes are the starting material commonly used in industrial hydroformylation reactions. Furthermore, the hydroformylation reaction of an olefin with functional groups such as a hydroxyl group (—OH) and a carboxyl group (—COOH) is also extremely important. For example, the hydroformylation of propylene alcohol and the subsequent reduction can produce 1,4-butanediol, which is an important raw material for synthetic polymers and other derivatives. In addition, functionalized internal olefins can be used as another synthetic route for difunctionalized building blocks in polymer synthesis. For example, the product produced by the hydroformylation of methyl 3-pentenoate is a raw material in the synthesis of polyamides and polyesters. In isomerization and hydroformylation reactions, high isomerization rate combined with high selectivity to form terminal aldehyde is an ideal reaction process, which not only reduce unnecessary hydrogenation, but also reduce the probability of isomerization to other conjugated compounds.

Many hydroformylation processes still utilize $PPh_3$ as ligands. Although the rhodium/triphenylphosphine system has been successfully implemented in factories all over the world, it limits the ratio of normal to isomeric (n/i) aldehyde products to about 10:1. In addition, the large amount of $PPh_3$ is not only poorly selective in the hydroformylation reaction, but also difficult in separation and posttreatment. In order to tackle these problems, transition-metal-bisphosphorous chelate complexes have been reported and patented by research groups and companies throughout the world. For example 2,2,-bis((diphenylphosphino)methyl)1,1-biphenyl (Bisbi) invented by Eastman; 6,6'-[3,) 3'-di-tert-butyl-5,5'-dimethoxy-1,1'-diphenyl-2,2'-diyl)bis(oxy)]bis(dibenzo[D,F][1,3,2]diphophos) (Biphephos) by Union Carbide (Buckwald); 4,5,-bisdiphenylphosphino-9,9-dimethylxanthene (Xantphos) and bidentate Diphosphoramidite by van Leeuween; 2,2'-bis((diarylphosphino)methyl)-1,1-binaphthyl (Naphos) by Matthias Belter and etc. The structures of these bidentate phosphorus ligands are illustrated as follows:

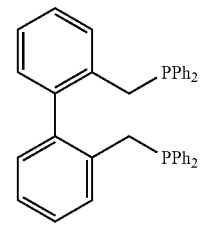

Bisbi
(Eastman)

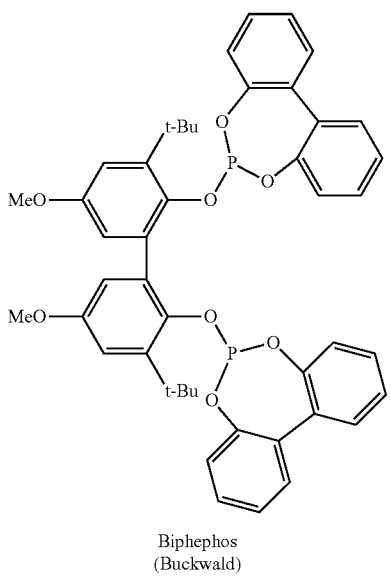

Biphephos
(Buckwald)

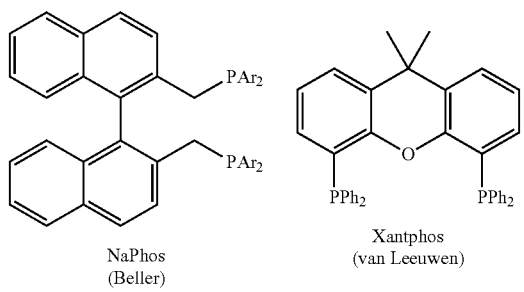

NaPhos
(Beller)

Xantphos
(van Leeuwen)

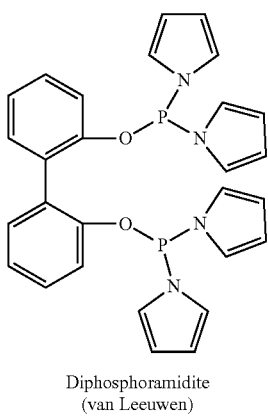

Diphosphoramidite
(van Leeuwen)

Using the above bidentate phosphorous ligand, a 400 times excess of PPh$_3$ can typically be reduced to only a 5 times excess of the chelated bidentate phosphorous ligand. This chelated bidentate phosphorous ligand has higher n/i (or l/b) ratio and catalytic activity in the hydroformylation reaction. For example, the n/i ratio of 1-hexene hydroformylation can be up to 70 to 120:1. Casey and van Leeuwen reported that the high selectivity with bisphosphorous ligand is due to the formation of a large bite angle (120 degree) between transition metal and ligand, i.e. The "Bite angle" theory, the structure is illustrated as follows:

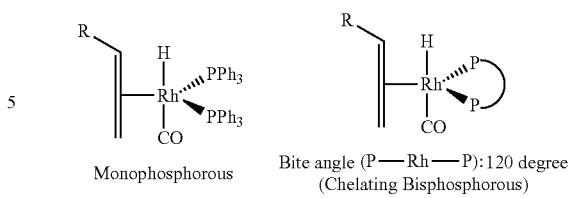

Monophosphorous

Bite angle (P—Rh—P):120 degree
(Chelating Bisphosphorous)

Although there are many reports on the use of bidentate phosphorous ligands for hydroformylation reactions, the development of higher selectivity and activity phosphorous ligands has been a research hotspot in the field of hydroformylation. However, it is difficult to achieve high normal to iso products (n/i) ratio due to the detachment of phosphorus during the coordination process of Rh-phosphorous complex and carbon monoxide molecule. Therefore, the development of multidentate phosphorous ligand with multi-chelating and coordination abilities is of great importance.

In addition to high selectivity, high isomerization speed is also a very important factor for the hydroformylation of internal olefins. The isomerization catalyst used in the present invention: Carbonylchlorohydrido[6-(di-tert-butyl-phosphinomethyl)-2-(N,N-diethylaminomethyl)pyridine]ruthenium(II), also known as Milstein Catalyst, its synthesis method and route was reported by the David Milstein (*J. Am. Chem. Soc.*, 2005, 127, 10840-10841). S. Perdriau et al. (*Chem. Eur. J.*, 2014, 47, 15434-15442) reported the use of RuH(Cl)(PNN)(CO) catalysts for isomerization of terminal olefins to internal olefins. These are the few reports on the isomerization of olefins with RuH(Cl)(PNN)(CO) catalyst Besides, there are few literatures on isomerization and hydroformylation to prepare linear aldehydes with rhodium-ruthenium dual metals.

Taking the 2-octenes hydroformylation as example, the Xantphos type ligand reported by van Leeuwen has a normal to iso products (n/i) ratio of 9.5 (*Angew. Chem. Int. Ed*, 1999. 38, 336). Beller reported a normal to iso products (n/i) ratio up to 10.1 with Naphos-type ligand (*Angew. Chem. Int. Ed.*, 2001, 40, 3408). The linear selectivity of ortho-phosphonate ligand in the octene mixture was 2.2 claimed by Börner (*Angew. Chem. Int. Ed.*, 2001, 40, 1696). The phosphinate ligands of Union Carbide Corp. (now Dow) have a normal to iso products ratio of: n/i=19 and 17 for 2-hexene and 2-octene respectively (U.S. Pat. No. 4,769,498). All literatures and patents mention above used rhodium as single metal catalyst.

The biphenyl tetradentate phosphine ligand (Tetrabi) used in the present invention has multiple chelating modes owing to its coordination ability. The hydroformylation of internal olefins is carried out in multi-chelating coordination modes with Rh-Tetrabi complex. Phosphine ligands are less likely to decompose from the Rh-Tetrabi catalyst system, and the steric hindrance effect of phosphines inhibits the formation of the isomeric aldehyde product, so that a high normal to iso products ratio is easily obtained. Therefore, the present invention utilizes a dual rhodium-ruthenium transition dual metals and metal-biphenyl tetradentate phosphine ligand as a catalytic system to obtain an unprecedented high normal to iso products ratio in the isomerization and hydroformylation of long-chain internal olefins.

SUMMARY

In view of the shortcomings of the low normal to iso products ratio of the aldehyde products in the existing internal olefin hydroformylation catalytic system, the technical problem to be solved by the present invention is to provide a catalyst which combines a rhodium-ruthenium dual metal with a tetradentate phosphine ligand, and a method of hydroformylation of internal olefins. The catalytic system of the invention has the advantages of high conversion rate, high normal to iso products ratio, stable catalyst at high temperature, and the etc.

The biphenyl tetradentate phosphine ligand according to the present invention, namely the chelating coordination mode of 2,2',6,6'-tetrakis(diarylphosphinomethyl)-1,1'-biphenyl (Tetraphosphine, or Tetrabi) and a transition metal rhodium, the structure is illustrated as follows:

naphthyl(Naphos), 4,5,-bisdiphenylphosphino-9,9-dimethyloxaxime(Xantphos), 6,6'-[(3,3'-di-tert-butyl-5,5'-dimethoxy-1,1'-diphenyl-2,2'-diyl) bis(oxygen))] bis[D, F][1,3,2] diphosphine dioxane) (Biphephos), 2,2'6,6', 4-tetrakis(diphenylphosphinomethyl)-1,1'-Biphenyl (Tetrabi) or other suitable phosphine source. Wherein the biphenyl tetraphosphine ligand used in the present invention, namely: 2,2',6,6'-tetrakis(diarylphosphonate methyl-1,1'-biphenyl (Tetrabi), has the optimal hydroformylation effect and a very high ratio of normal to iso products when compared with the above phosphine ligands. The structure of the compound and its derivatives is illustrated as follows:

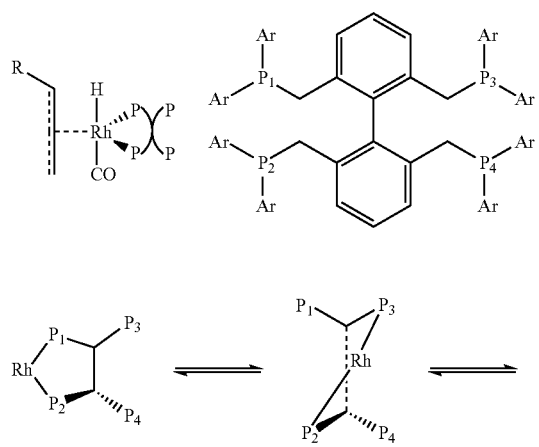

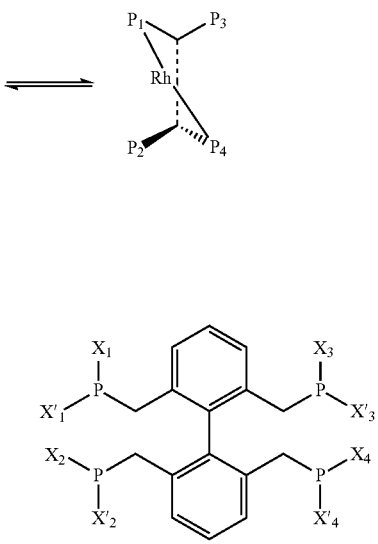

Four different chelating modes between Rh and tetraphospine.

The present invention provides a novel catalyst for isomerization and hydroformylation of internal olefins, consisting of a rhodium complex and a ruthenium compound, is the rhodium complex is formed by completing a rhodium compound with a biphenyl tetraphosphosphine ligand.

The above catalyst, in which the molar ratio of the rhodium complex to the ruthenium compound is ranged from 1:1 to 5:1, and the molar ratio of the biphenyl tetraphosphine ligand to the rhodium compound is ranged from 1:1 to 10:1.

The ruthenium compound may be Rhodium trichloride ($RhCl_3$), (bicyclo [2.2.1] hepta-2,5-diene) chloro rhodium (I) dimer (($Rh(NBD)Cl)_2$), Chloro (1,5-cyclooctadiene) rhodium (I) dimer ($Rh(COD)Cl)_2$), Chloro di(ethylene) rhodium dimer (($Rh(ethylene)_2Cl)_2$), Tris(triphenylphosphine) rhodium ($RhCl(PPh_3)_3$), Rhodium carbonyl chloride (($Rh(CO)_2Cl)_2$), Dicarbonylacetylacetonato rhodium (I) ($Rh(acac)(CO)_2$), acetylacetonato (1,5-cyclooctadiene) rhodium (I) ($Rh(acac)(COD)$), Rhodium carbonyl ($Rd_6(CO)_{16}$ or $Rh_4(CO)_{12}$), Rhodium acetate (II) ($Rh_2(OAc)_4$), Rhodium(III) nitrate ($Rh(NO_3)_3$) or other appropriate rhodium compound, preferably Dicarbonylacetylacetonato rhodium (I).

In the hydroformylation reaction, the concentration of the ruthenium compound is ranged from 50 to 1,500 ppm, and preferably from 100 to 800 ppm.

The organophosphine ligand has a monophosphine ligand such as triphenylphosphine ($PPh_3$) triphenyl phosphinate ($P(OC_6H_5)_3$), etc., and may also be a polydentate phosphine ligand such as 2,2'-di(((diphenylphosphino)methyl)-1,1'-biphenyl (Bisbi), 2,2',6-tris(diphenylphosphinomethyl)-1,1'-biphenyl (Tribi), 2,2'-bis((diarylphosphino)methyl)-1,1-bi- $X_{1,2,3,4} X'_{1,2,3,4}$ = Ar, R, OR, OAr, pyrrole, substituted pyrrole In the formula II, Ar may be benzene, m-trifluoromethylbenzene, 3,5-ditrifluoromethylbenzene, p-methylbenzene, p-trifluoromethylbenzene, 3,5-difluorobenzene, 3,5-dimethylbenzene, 3,5-di-tert-butylbenzene, 3,5-di-tert-butyl-4-methoxybenzene, p-methoxybenzene, p-dimethylaminobenzene, 2-pyridine, p-fluorobenzene, 2,3,4,5,6-pentafluorobenzene, tert-butyl, pyrrole and indole, the structures of which are as follows:

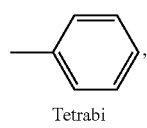

Tetrabi

L2 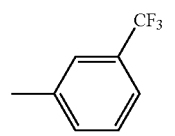

L3 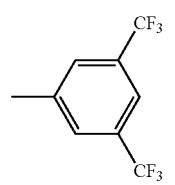

L4 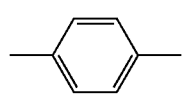

L5 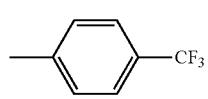

L6 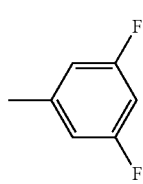

L7 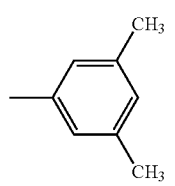

L8 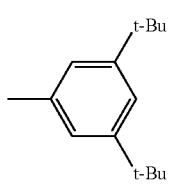

L9 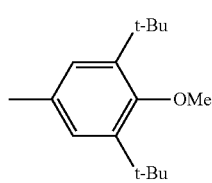

L10 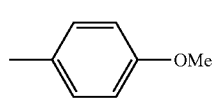

L11 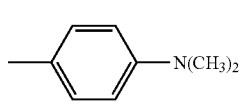

L12 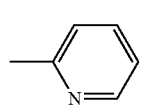

L13 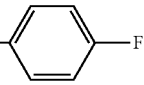

L14 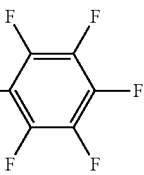

L15 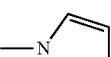

L16 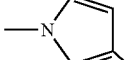

L17 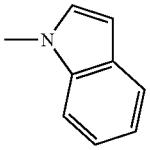

The ruthenium compound may be ruthenium carbonyl ($Ru_3(CO)_{12}$), ruthenium trichloride ($RuCl_3$), tris(triphenylphosphine) ruthenium (II) chloride ($RuCl_2(PPh_3)_3$), dichloro Tricarbonyl ruthenium dimer (($RuCl_2(CO)_3)_2$), tris(triphenylphosphine)carbonylindoline (II) ($RuH_2(CO)PPh_3)_3$), (1,5-cyclooctane Ethylene ruthenium(II) dichloride (($RuCl_2(COD)_n$), bis-(2-methylallyl)cyclooctane-1,5-dienyl ruthenium ($Ru(COD)(methallyl)_2$), Carbonylchlorohydrido [6-(di-tert-butylphosphinomethyl)-2-(N,N-diethylaminomethyl)pyridine] ruthenium (II), Carbonylhydrido[6-(di-t-butylphosphinomethylene)-2-(N,N-diethylaminomethyl)-1,6-dihydropyridine] ruthenium (II) (RuH (PNN) (CO)) or other appropriate ruthenium compounds Preferably, Carbonylchlorohydrido[6-(di-tert-butylphosphinomethyl)-2-(N,N-diethylaminomethyl)pyridine] ruthenium (II) (RuH(Cl)(PNN)(CO)).

In the isomerization and hydroformylation reaction, the concentration of the ruthenium compound is ranged from 10 to 2000 ppm, and 100 to 1000 ppm is preferred.

The preparation method of the internal olefin isomerization and hydroformylation catalyst of the present invention is as follows:

Stirring the weighted rhodium catalyst precursor and the biphenyl tetradentate phosphine ligand at room temperature for 30 to 90 min in an organic solvent under inert gas protection (anhydrous and deoxygenated condition); and then add the ruthenium catalyst into the rhodium-ligand complex solution and stirring at room temperature for 15 to 30 min.

The steps of the olefin isomerization and hydroformylation experiments of the present invention under the rhodium-ruthenium dual metal and biphenyl tetraphosphine ligand catalytic system are: first, under inert gas protection, transferring certain amount of the completed rhodium-ruthenium catalyst solution, certain amount of internal standard n-decane and isopropanol as an additive, certain amount of solvent, and finally the substrate-internal olefin into a reaction flask equipped with a magnetic stirrer, after the transfer is completed, charging certain amount of CO and $H_2$ into the autoclave containing the reaction flask. The pressure ratio of hydrogen to carbon monoxide is between 1.5:1 to 10:1, which is optimally 1:1, the total pressure is between 0.2 MPa and 4 MPa, of which 0.4 MPa to 1 MPa is preferred; finally, at an oil bath temperature between 8° C. and 140° C. which is optimal at 120° C. to 140° C., reacting with stirring for 1 to 12 hours, preferably 1 hour to 4 hours.

In the reaction process for the purpose of not evaluating the catalytic effect, it is unnecessary to add an internal standard. With isopropanol as an additive, the ruthenium catalyst accelerates the isomerization rate of internal olefins in isopropanol.

The internal olefin substrate used in the present invention is 2-octene (cis, trans mixture), and the composition of the cis, trans-2-octene is determined by gas chromatography, 19.5% of the mixture component is cis-2-octene, and 80.5% of the mixture component is trans-2-octene. The ratio of the amount of the rhodium-based compound to the reactant is between 0.005 and 0.15 mol %, and preferably 0.01 to 0.08 mol %. The molar ratio of the organic phosphine ligand to the rhodium-based compound is between 1:1 and 10:1, preferably 4:1 and 6:1.

The gas chromatography analysis method according to the present invention comprises the following steps: (1) preparing a mixed solution of 2-octene (cis-mixed mixture) and n-decane in different concentration ratios, and calculating correction factor K of internal standard and 2 octene (cis, trans mixture) by GC analysis; (2) analyzing by gas chromatography with RTX-5 as stationary phase, flame ionization detection, setting split ratio to 20, injection port temperature to 250° C., detector temperature to 260° C., column initial column temperature to 60° C. keep for 8 minutes, and then raising to a column temperature of 120-180° C. at a speed of 5° C./min, the above analytical method can ensure complete separation of high boiling aldehyde products from the chromatogram column; (3) obtaining the linear aldehyde percentage by finding the integral of the corresponding peak according to the peak time of the aldehyde product n-nonanal (a-aldehyde) and 2-methyl octanal (β-aldehyde); (4) calculate the peak area according to the peak time of the reactant 2-octene (cis, trans mixture) and the internal standard, and calculate the conversion rate, the number of conversion, etc., and in combination with the correction factor.

The organic solvent applicable for the above catalytic reaction process may be methylbenzene, dichloromethane, dichloroethane, hexane, ethyl acetate, methanol, ethanol isopropanol, trifluoroethanol, dioxane, acetonitrile, tetrahydrofuran, etc. The alcohol solvent is particularly effective for the dual metal catalyst of the present invention.

Internal olefins applicable for the dual metal catalytic homogeneous system of the present invention, from $C_4$ to $C_8$ are: 2-butene, cis, trans-2-pentene, cis, trans-2-hexene, cis, trans-3-hexene, cis, trans-2-heptene, cis, trans-3-heptene, cis, trans-2-octene, cis, trans-3-octene, cis, trans-4-octene.

The catalytic system of the rhodium-ruthenium dual metal complex described in the present invention combined with the biphenyl tetraphosphine ligand has an unprecedented high normal aldehyde to isomeric aldehyde ratio, high conversion rate (high conversion number), stable catalyst at high temperature and industrial amplification, etc., when compared with the hydroformylation reaction results of long-chain internal olefin ($\geq C_8$) in all literatures and patents domestic and abroad.

Since internal olefins are more prone to produce by-products such as branched aldehydes and branched paraffins than end olefins, and the hydroformylation effect is more complicated, the aldehyde products are relatively low in normal to iso product ratio. The industrial large-scale hydroformylation process utilizes low-cost mixed internal olefins and terminal olefins as olefin feedstocks, wherein there are more internal olefins and fewer terminal olefins, so the method provided by the present invention has greater industrial application value.

DESCRIPTION OF THE EMBODIMENTS

The following description is of preferred embodiments by way of example only and without limitation to the combination of features necessary for carrying the invention into effect. However, it should be noted that the present invention is by no means limited or restricted to the below described embodiments and the implementation features thereof but comprises further modifications of the embodiments, in particular those that are comprised by modifications of the features of the described examples and/or by combination of one or more features of the described examples on the basis of the scope of protection of the independent claims.

Example 1: Isomerization and hydroformylation (S/C=2000, S/C is the molar ratio of reactant to catalyst) using rhodium-ruthenium dual metal (Rh (acac) $(CO)_2$ RuH (Cl) (PNN) (CO)) and biphenyl triphosphine ligand (Tribi), rhodium-ruthenium (Rh(acac)$(CO)_2$, RuH(Cl)(PNN)(CO)) and biphenyl tetraphosphine ligand (Tetrabi)

Rh, Ru+Tribi: Weighing the catalyst Rh(acac)$(CO)_2$ (5.2 mg, 0.02 mmol) and 2,2',6-tris(diphenylphosphinomethyl)-1,1'-Biphenyl (Tribi) (60 mg, 0.08 mmol) with a glove box into a complex flask, and then placing the deoxygenated/dewatered dichloromethane (2.65 g, 31.2 mmol) solvent into a flask, stirring to dissolve them to obtain a complex of rhodium and biphenyl triphosphine ligand. Subsequently, weighing a ruthenium catalyst RuH(Cl)(PNN)(CO) (9.8 mg, 0.02 mmol) with a glove box, adding it to the complexed rhodium catalyst solution, and stirring at room temperature to dissolve them. Placing the autoclave into the glove box, using a micro syringe to transfer 100 μl of the complexed rhodium-ruthenium catalyst solution into a reaction flask (5 ml) with magnetic stirrer, and adding 100 μl of the internal standard n-decane, 150 μl of additive, 350 μl of solvent and 2-octene (cis, trans mixture) (224.4 mg, 2 mmol). Then, taking the autoclave containing the reaction flask out from the glove box, and replacing the high-purity argon gas in the vessel with $H_2$ three times, raising the total pressure of the autoclave to 4 bar at a CO/$H_2$ pressure ratio of 1:1, and then placing the autoclave at oil bath temperature 140° C. and stirring for 1 hour and 4 hours, respectively.

Rh, Ru+Tetrabi: Weighing the catalyst Rh(acac)$(CO)_2$ (5.2 mg, 0.02 mmol), 2,2',6,6'-tetrakis(diphenylphosphinomethyl)-1,1'-biphenyl (Tetrabi) (76 mg, 0.08 mmol) with a glove box and placing them into a complex flask, then adding deoxygenated/dewatered (2.65 g, 31.2 mmol) into the flask and stirring to dissolve them to obtain a complex solution of rhodium and biphenyl tetraphosphine ligand. Subsequently, weighing the ruthenium catalyst RuH(Cl) (PNN)(CO) (9.8 mg, 0.02 mmol) with a glove box and adding it into the complexed rhodium catalyst solution, stiring at room temperature to dissolve them. Placing the autoclave into the glove box, using a micro syringe to transfer 100 μl of the complexed rhodium-ruthenium catalyst solution into a reaction flask (5 ml) with magnetic stirrer, and adding 100 μl internal standard n-decane, 150 μl additive and 350 μl solvent, and finally 2-octene (cis, trans mixture) (224.4 mg, 2 mmol). Then, taking the autoclave containing the reaction flask out from the glove box, and replacing the high-purity argon gas in the vessel with $H_2$ three times, raising the total pressure of the autoclave to 4 bar at a CO/$H_2$ pressure ratio of 1:1, and then placing the autoclave at oil bath temperature 140° C. and stirring for 1 hour and 4 hours, respectively.

TABLE 1

$n\text{-}C_5H_{11}$ ╱╲╱ + $n\text{-}C_5H_{11}$ ╱╲╲ →(L/Rh, L/Ru, S/C = 2000; CO/H$_2$ = 2.0:2.0 bar; 140° C., Solvent)→ $n\text{-}C_5H_{11}$-CH$_2$CH$_2$CHO (l) + $n\text{-}C_5H_{11}$-CH(CH$_3$)CHO (b)

| No. | solvent | ligand | L/Rh L/Ru | Time [h] | Conversion rate[%] | l/b [%] | Linearity [%] | TON |
|---|---|---|---|---|---|---|---|---|
| 1 | ethanol | Tribi | 4:1 | 1 | 39.7 | 31.3 | 96.9 | $7.9 \times 10^2$ |
| 2 | ethanol | Tribi | 4:1 | 4 | 78.6 | 34.7 | 97.2 | $1.6 \times 10^3$ |
| 3 | ethanol | Tetrabi | 4:1 | 1 | 68.8 | 65.8 | 98.5 | $1.4 \times 10^3$ |
| 4 | ethanol | Tetrabi | 4:1 | 4 | 87.2 | 43.9 | 97.8 | $1.7 \times 10^3$ |
| 5 | methanol | Tribi | 4:1 | 1 | 53.8 | 61.8 | 98.4 | $1.1 \times 10^3$ |
| 6 | methanol | Tribi | 4:1 | 4 | 81.3 | 46.8 | 97.9 | $1.6 \times 10^3$ |
| 7 | methanol | Tetrabi | 4:1 | 1 | 79.6 | 82.3 | 98.8 | $1.6 \times 10^3$ |
| 8 | methanol | Tetrabi | 4:1 | 4 | 90.8 | 60.0 | 98.4 | $1.8 \times 10^3$ |
| 9 | trifluoroethanol | Tribi | 4:1 | 1 | 61.2 | 69.4 | 98.6 | $1.2 \times 10^3$ |
| 10 | trifluoroethanol | Tribi | 4:1 | 4 | 78.7 | 58.6 | 98.3 | $1.6 \times 10^3$ |
| 11 | trifluoroethanol | Tetrabi | 4:1 | 1 | 73.6 | 141.9 | 99.3 | $1.5 \times 10^3$ |
| 12 | trifluoroethanol | Tetrabi | 4:1 | 4 | 93.6 | 61.6 | 98.4 | $1.9 \times 10^3$ |

Example 2: Isomerization and hydroformylation (S/C=4000) using rhodium-ruthenium dual metal (Rh(acac)(CO)$_2$, RuH(Cl)(PNN)(CO)) and biphenyl triphosphine ligand (Tribi), rhodium-ruthenium dual metal (Rh(acac)(CO)$_2$, RuH(Cl)(PNN)(CO)) and biphenyl tetraphosphine ligand (Tetrabi)

Rh, Ru+Tribi: Weighing the catalyst Rh(acac)(CO)$_2$ (2.6 mg, 0.01 mmol), 2,2',6-Tris(diphenylphosphinomethyl)-1,1'-biphenyl (Tribi) (30 mg, 0.04 mmol) within a glove box and placing them into a complex flask, then adding deoxygenated/dewatered dichloromethane (2.65 g, 31.2 mmol) into the flask, and stirring to dissolve them to obtain a complexed solution of rhodium and biphenyl triphosphine ligand. Subsequently, weighing the ruthenium catalyst RuH(Cl)(PNN)(CO) (4.9 mg, 0.01 mmol) within a glove box and adding it into the complexed rhodium catalyst solution at room temperature. Placing the autoclave into the glove box, using a micro syringe to transfer 100 µl of the complexed rhodium-ruthenium catalyst solution into reaction flask (5 ml) with magnetic stirrer, and adding 100 µl of the internal standard n-decane, 150 µl additive and 350 µl of solvent, and finally 2-octene (cis, trans mixture) (224.4 mg, 2 mmol). Then, taking the autoclave containing the reaction flask out from the glove box, and replacing the high-purity argon gas in the vessel with H$_2$ three times, raising the total pressure of the autoclave to 4 bar at a CO/H$_2$ pressure ratio of 1:1, and then placing the autoclave at oil bath temperature 140° C. and stirring for 1 hour and 4 hours, respectively.

Rh, Ru+Tetrabi: Weighing the catalyst Rh(acac)(CO)$_2$ (2.6 mg, 0.01 mmol), 2,2',6,6'-tetrakis(diphenylphosphinomethyl)-1,1'-biphenyl (Tetrabi) (38 mg, 0.04 mmol) within a glove box and placing them into a complex flask, then adding deoxygenated/dewatered dichloromethane (2.65 g, 31.2 mmol) in a complex flask and stirring to dissolve them to obtain a complex solution of rhodium and biphenyl tetraphosphine ligand. Subsequently, weighing the ruthenium catalyst RuH(Cl)(PNN)(CO) (4.9 mg, 0.01 mmol) within a glove box and adding it into the complexed rhodium catalyst solution at room temperature. Placing the autoclave into the glove box, using a micro syringe to transfer 100 µl of the complexed rhodium-ruthenium catalyst solution into a reaction flask (5 ml) with magnetic stirrer, and adding 100 µl of internal standard n-decane. 150 µl additive and 350 µl solvent, and finally 2-octene (cis, trans mixture) (224.4 mg, 2 mmol). Then, taking the autoclave containing the reaction flask out from the glove box, and replacing the high-purity argon gas in the vessel with H$_2$ three times, raising the total pressure of the autoclave to 4 bar at a CO/H$_2$ pressure ratio of 1:1, and then placing the autoclave at oil bath temperature 140° C. and stirring for 1 hour and 4 hours, respectively.

TABLE 2

$n\text{-}C_5H_{11}$ ╱╲╱ + $n\text{-}C_5H_{11}$ ╱╲╲ →(L/Rh, L/Ru, S/C = 4000; CO/H$_2$ = 2.0:2.0 bar; 140° C., Solvent)→ $n\text{-}C_5H_{11}$-CH$_2$CH$_2$CHO (l) + $n\text{-}C_5H_{11}$-CH(CH$_3$)CHO (b)

| No. | solvent | ligand | L/Rh L/Ru | Time [h] | conversion rate[%] | l/b [%] | Linearity [%] | TON |
|---|---|---|---|---|---|---|---|---|
| 1 | ethanol | Tribi | 4:1 | 1 | 17.6 | 13.7 | 93.2 | $7.0 \times 10^2$ |
| 2 | ethanol | Tribi | 4:1 | 4 | 50.4 | 15.9 | 94.1 | $2.0 \times 10^3$ |
| 3 | ethanol | Tetrabi | 4:1 | 1 | 27.8 | 32.3 | 97.0 | $1.1 \times 10^3$ |
| 4 | ethanol | Tetrabi | 4:1 | 4 | 59.7 | 37.5 | 97.4 | $1.5 \times 10^3$ |
| 5 | methanol | Tribi | 4:1 | 1 | 44.3 | 51.7 | 98.1 | $1.8 \times 10^3$ |
| 6 | methanol | Tribi | 4:1 | 4 | 65.0 | 32.5 | 97.0 | $2.6 \times 10^3$ |
| 7 | methanol | Tetrabi | 4:1 | 1 | 68.2 | 92.8 | 98.9 | $2.7 \times 10^3$ |
| 8 | methanol | Tetrabi | 4:1 | 4 | 81.4 | 78.0 | 98.7 | $3.3 \times 10^3$ |
| 9 | trifluoroethanol | Tribi | 4:1 | 1 | 44.5 | 76.2 | 98.7 | $1.8 \times 10^3$ |
| 10 | trifluoroethanol | Tribi | 4:1 | 4 | 65.4 | 46.8 | 97.9 | $2.6 \times 10^3$ |
| 11 | trifluoroethanol | Tetrabi | 4:1 | 1 | 63.7 | 93.8 | 98.9 | $2.5 \times 10^3$ |
| 12 | trifluoroethanol | Tetrabi | 4:1 | 4 | 81.6 | 59.5 | 98.3 | $3.3 \times 10^3$ |

Example 3: Isomerization and hydroformylation (S/C=10000) using rhodium-ruthenium dual metal (Rh (acac)(CO)$_2$, RuH(Cl)(PNN)(CO)) and biphenyl triphosphine ligand (Tribi), rhodium-ruthenium dual metal (Rh (acac)(CO)$_2$, RuH(Cl)(PNN)(CO)) and biphenyl tetraphosphine ligand (Tetrabi)

Rh, Ru+Tribi: Weighing the catalyst Rh(acac)(CO)$_2$ (2.6 mg, 0.01 mmol), 2,2',6-Tris(diphenylphosphinomethyl)-1,1'-biphenyl (Tribi) (30 mg, 0.04 mmol) within a glove box and placing them into a complex flask, then adding deoxygenated/dewatered dichloromethane (6.63 g, 78.0 mmol) in a flask and stirring lo dissolve them to obtain a complex solution of rhodium and biphenyl triphosphine ligand. Subsequently, weighing a ruthenium catalyst RuH(Cl)(PNN)(CO) (4.9 mg, 0.01 mmol) within a glove box, adding it to the complexed rhodium catalyst solution, and stirring to dissolve them at room temperature. Placing the autoclave into the glove box, using a micro syringe to transfer 100 μl of the complexed rhodium-ruthenium catalyst solution into a reaction flask (5 ml) with magnetic stirrer, and adding 100 μl of internal standard n-decane, 150 μl of additive and 350 μl of solvent, and finally 2-octene (cis, trans mixture) (224.4 mg, 2 mmol). Then, taking the autoclave containing the reaction flask out from the glove box, and replacing the high-purity argon gas in the vessel with H$_2$ three times, raising the total pressure of the autoclave to 4 bar at a CO/H$_2$ pressure ratio of 1:1, and then placing the autoclave at oil bath temperature 140° C. and stirring for 1 hour and 4 hours, respectively.

Rh, Ru+Tetrabi: Weighing the catalyst Rh(acac)(CO)$_2$ (2.6 mg, 0.01 mmol). 2,2',6,6'-tetrakis(diphenylphosphinomethyl)-1,1'-biphenyl (Tetrabi) (38 mg, 0.04 mmol) within a glove box and placing them into a complex flask, then adding deoxygenated/dewatered dichloromethane (6.63 g, 78.0 mmol) in a complex flask and stirring to dissolve them to obtain a complex solution of rhodium and biphenyl tetraphosphine ligand. Subsequently, weighing the ruthenium catalyst RuH(Cl)(PNN)(CO) (4.9 mg, 0.01 mmol) within a glove box and adding it into the complexed rhodium catalyst solution at room temperature. Placing the autoclave into the glove box, using a micro syringe to transfer 100 μl of the complexed rhodium-ruthenium catalyst solution into a reaction flask (5 ml) with magnetic stirrer, and adding 100 μl of the internal standard n-decane, adding 150 μl of additive and 350 μl of solvent, finally 2-octene (cis-mixture) (224.4 mg, 2 mmol). Then, taking the autoclave containing the reaction flask out from the glove box, and replacing the high-purity argon gas in the vessel with H$_2$ three times, raising the total pressure of the autoclave to 4 bar at a CO/H$_2$ pressure ratio of 1:1, and then placing the autoclave at oil bath temperature 140° C. and stirring for 1 hour and 4 hours, respectively.

TABLE 3 n-C$_5$H$_{11}$⟶ + n-C$_5$H$_{11}$⟶ (L/Rh, L/Ru, S/C = 10000; CO/H$_2$ = 2.0:2.0 bar; 140° C., Solvent) → n-C$_5$H$_{11}$—CHO (l) + n-C$_5$H$_{11}$—CHO (b)

| No. | solvent | ligand | L/Rh L/Ru | Time [h] | conversion rate[%] | l/b [%] | Linearity [%] | TON |
|---|---|---|---|---|---|---|---|---|
| 1 | ethanol | Tribi | 4:1 | 1 | 8.2 | 12.7 | 92.7 | 8.2 × 10$^2$ |
| 2 | ethanol | Tribi | 4:1 | 4 | 26.4 | 15.4 | 93.6 | 2.6 × 10$^3$ |
| 3 | ethanol | Tetrabi | 4:1 | 1 | 18.9 | 33.7 | 97.1 | 1.9 × 10$^3$ |
| 4 | ethanol | Tetrabi | 4:1 | 4 | 36.1 | 31.0 | 96.9 | 3.6 × 10$^3$ |
| 5 | methanol | Tribi | 4:1 | 1 | 20.0 | 35.2 | 97.3 | 2.2 × 10$^3$ |
| 6 | methanol | Tribi | 4:1 | 4 | 60.8 | 28.4 | 96.6 | 6.1 × 10$^3$ |
| 7 | methanol | Tetrabi | 4:1 | 1 | 41.1 | 72.5 | 98.6 | 4.1 × 10$^3$ |
| 8 | methanol | Tetrabi | 4:1 | 4 | 79.4 | 58.2 | 98.3 | 7.9 × 10$^3$ |
| 9 | trifluoroethanol | Tribi | 4:1 | 1 | 11.7 | 42.6 | 97.7 | 1.2 × 10$^3$ |
| 10 | trifluoroethanol | Tribi | 4:1 | 4 | 31.5 | 27.6 | 96.5 | 3.2 × 10$^3$ |
| 11 | trifluoroethanol | Tetrabi | 4:1 | 1 | 28.0 | 79.7 | 98.7 | 2.8 × 10$^3$ |
| 12 | trifluoroethanol | Tetrabi | 4:1 | 4 | 47.5 | 42.5 | 97.7 | 4.8 × 10$^3$ |

Example 4: Isomerization and hydroformylation (S/C=10000) using rhodium-ruthenium dual metal (Rh (acac)(CO)$_2$, RuH(Cl)(PNN)(CO)) and biphenyl triphosphine ligand (Tribi), rhodium-ruthenium dual metal (Rh (acac)) (CO)$_2$, RuH(Cl)(PNN)(CO)) and biphenyl tetraphosphine ligand (Tetrabi) (comparison of various α-, β-, γ-olefin results)

Rh, Ru+Tribi: Weighing the catalyst Rh(acac)(CO)$_2$ (2.6 mg, 0.01 mmol), 2,2',6-tris(diphenylphosphinomethyl)-1,1'-Biphenyl (30 mg, 0.04 mmol) within a glove box and placing them into a complex flask, and then adding deoxygenated/dewatered dichloromethane (1.33 g, 15.6 mmol) solvent into the flask, stirring to dissolve them to obtain a complex solution of rhodium and biphenyl triphosphine ligand. Subsequently, weighing a ruthenium catalyst RuH(Cl)(PNN)(CO) (4.9 mg, 0.01 mmol) within a glove box, adding it to the complexed rhodium catalyst solution, and stirring at room temperature to dissolve them. Placing the autoclaves into the glove box, using a micro syringe to transfer 100 μl of the complexed rhodium-ruthenium catalyst solution into a reaction flask (5 ml) with magnetic stirrer, and adding 100 μl of the internal standard n-decane, appropriate amount of additives and corresponding solvents, and finally various α-, β-, γ- olefin (1 mmol) in batches. Then, taking the autoclaves containing the reaction flasks out from the glove box, and replacing the high-purity argon gas in the vessels with H$_2$ three times, raising the total pressure of the autoclaves to 4 bar at a CO/H$_2$ pressure ratio of 1:1, and then placing the autoclaves at oil bath temperature 140 ° C. and stirring for 2 hours.

Rh, Ru+Tetrabi: Weighing the catalyst Rh(acac)(CO)$_2$ (2.6 mg, 0.01 mmol), 2',6,6'-tetrakis(diphenylphosphinomethyl)-1,1'Biphenyl (Tetrabi) (38 mg, 0.04 mmol) within a glove box and placing them into a complex flask, and then adding deoxygenated/dewatered toluene (0.87 g, 9.4 mmol) into the flask and stirring to dissolve to obtain a complex solution of rhodium and biphenyl tetraphosphine ligand. Subsequently, weighing a ruthenium catalyst RuH(Cl)(PNN)(CO) (4.9 mg, 0.01 mmol) within a glove box, adding it to the complexed rhodium catalyst solution, and stirring at room temperature to dissolve them. Placing the autoclaves into the glove box, using a micro syringe to transfer 100 μl of the complexed rhodium-ruthenium catalyst solution into the reaction flask (5 ml) with magnetic stirrer, and adding 100 μl internal standard n-decane, appropriate amount of additives and corresponding solvents, and finally various α-, β-, γ- olefin (1 mmol) in batches. Then, taking the autoclaves containing the reaction flasks out from the glove box, and replacing the high-purity argon gas in the vessels with $H_2$ three times, raising the total pressure of the autoclaves to 4 bar at a $CO/H_2$ pressure ratio of 1:1, and then placing the autoclaves at oil bath temperature 140° C. and stirring for 2 hours.

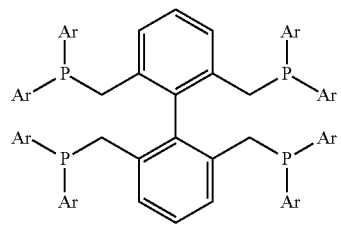

I in formula 1, Ar is selected from a group consisting of: benzene, p-methylbenzene, m-trifluoromethylbenzene,

TABLE 4

| No. | substrate | ligand | conversion rate[%] | l/b [%] | linearity [%] | Isomerization [%] | TON |
|---|---|---|---|---|---|---|---|
| 1 | Trans-2-hexene | Tribi | 59.2 | 22.8 | 95.8 | 9.9 | $5.9 \times 10^2$ |
| 2 | Trans-2-hexene | Tetrabi | 60.8 | 39.0 | 97.5 | 12.8 | $6.1 \times 10^2$ |
| 3 | Cis-2-hexene | Tribi | 81.9 | 75.9 | 98.7 | 47.3 | $8.2 \times 10^2$ |
| 4 | Cis-2-hexene | Tetrabi | 85.1 | 82.3 | 98.8 | 61.5 | $8.5 \times 10^2$ |
| 5 | Cis, trans-2-octene | Tribi | 72.5 | 99.0 | 99.0 | 1.8 | $7.3 \times 10^2$ |
| 6 | Cis, trans-2-octene | Tetrabi | 80.4 | 110.1 | 99.1 | 2.6 | $8.0 \times 10^2$ |
| 7 | Cis, trans-2-nonylene | Tribi | 61.1 | 44.5 | 97.8 | 32.4 | $6.1 \times 10^2$ |
| 8 | Cis, trans-2-nonylene | Tetrabi | 82.8 | 65.7 | 98.5 | 64.3 | $8.3 \times 10^2$ |
| 9 | Trans-3-hexene | Tribi | 55.2 | 8.4 | 89.4 | 9.5 | $5.5 \times 10^2$ |
| 10 | Trans-3-hexene | Tetrabi | 49.6 | 65.7 | 98.5 | 13.9 | $5.0 \times 10^2$ |
| 11 | Trans-3-octene | Tribi | 67.8 | 11.8 | 92.2 | 50.7 | $6.8 \times 10^2$ |
| 12 | Trans-3-octene | Tetrabi | 78.1 | 44.5 | 97.8 | 46.6 | $7.8 \times 10^2$ |
| 13 | Cis-4-octene | Tribi | 64.2 | 10.1 | 91.0 | 48.3 | $6.4 \times 10^2$ |
| 14 | Cis-4-octene | Tetrabi | 72.9 | 61.5 | 98.4 | 47.9 | $7.3 \times 10^2$ |
| 15 | Cis, trans-4-octene | Tribi | 46.7 | 4.6 | 82.0 | 12.1 | $4.7 \times 10^2$ |
| 16 | Cis, trans-4-octene | Tetrabi | 59.3 | 57.8 | 98.3 | 27.7 | $5.9 \times 10^2$ |

What is claimed is:

1. A catalyst comprising a rhodium complex and a ruthenium compound, wherein the rhodium complex is formed by complexing a rhodium compound with a biphenyl tetraphosphine ligand, and the ruthenium compound does not complex with the biphenyl tetraphosphine ligand, the rhodium compound and the rhodium complex.

2. The catalyst according to claim 1, wherein the molar ratio of the rhodium complex to the ruthenium compound is ranged from 1:1 to 5:1, and the molar ratio of the biphenyl tetraphosphine ligand to the rhodium compound is ranged from 1:1 to 10:1.

3. The catalyst according to claim 1, wherein the rhodium compound is selected from a group consisting of: $RhCl_3$, $(Rh(NBD)Cl)_2$, $(Rh(COD)Cl)_2$, $(RH(ethylene)_2(Cl))_2$, $RhCl(PPh_3)_3$, $(Rh(CO)_2Cl)_2$, $Rh(acac)(CO)_2$, $Rh(acac)(COD)$, $Rh_6(CO)_{12}$, $Rh_4(CO)_{12}$, $Rh_2(OAc)_4$, $Rh(NO_3)_3$, $(Rh(NBD)_2)X$ and $(Rh(COD)_2)X$, wherein X is a conjugated anion, NBD is a bicycloheptadiene; and COD is cyclooctadiene.

4. The catalyst according to claim 1, wherein the biphenyl tetraphosphine ligand has a structure illustrated as follows:

p-trifluoromethylbenzene, 3,5-ditrifluoromethylbenzene, 3,5-difluorobenzene, 3,5-dimethylbenzene, 3,5-di-tert-butylbenzene, 3,5-di-tert-butyl-4-methoxybenzene, p-methoxybenzene, p-dimethylaminobenzene, 2-pyridine, p-fluorobenzene, and 2,3,4,5,6-pentafluorobenzene.

5. The catalyst according to claim 1, wherein the ruthenium compound is selected from a group consisting of: $Ru_3(CO)_{12}$, $RuCl_3$, $RuCl_2(PPh_3)_3$, $(RuCl_2(CO)_3)_2$, $RuH(CO)_2(PPh_3)_3$, $Ru(Ar)X_2$, $Ru(ArH)Cl_2$, $Ru(Ar)X_2(PPh_3)_3$, $Ru(COD)(COT)$, $Ru(COD)(COT)X$, $Ru(COD)_n$, $RuCl_2(COD)$, $(Ru(COD)_2)X$, $(RuCl_2(COD))_n$, $Ru(COD)(methallyl)_2$, $RuX_2(cymene)$, $RuX_2(PN)$, $RuX_2(PN)$, $RuH(Cl)(PNN)(CO)$, and $RuH(PNN)(CO)$, wherein Ar is a group having an aromatic ring; X is a conjugated anion, COD is cyclooctadiene; and COT is cyclooctadiene.

6. A reaction method for isomerization and hydroformylation of internal olefins, comprising:

first, under inert gas protection, transferring certain amount of a complexed rhodium-ruthenium catalyst solution, certain amount of isopropanol as an additive, certain amount of solvent, and finally a substrate-internal olefin into a reaction flask equipped with a magnetic stirrer; wherein the complexed rhodium-ruthenium catalyst solution comprises a rhodium complex and a ruthenium compound, the rhodium complex is formed by complexing a rhodium compound with a biphenyl tetraphosphine ligand, and the ruthenium compound does not complex with the biphenyl tetraphosphine ligand, the rhodium compound and the rhodium complex;

second, charging certain amount of CO and $H_2$ with a certain pressure into a autoclave containing the reaction flask, and wherein a pressure ratio of $H_2$ to CO is ranged between 1.5:1 and 10:1, and the total pressure is ranged from 0.2 MPa to 4 MPa: and placing the autoclave at oil bath temperature between 80° C. and 140° C. and stirring for 1 to 12 hours.

7. The reaction method according to claim 6, wherein the organic solvent is selected from a group consisting of: methylbenzene, dichloromethane, dichloroethane, hexane, ethyl acetate, methanol, ethanol, trifluoroethanol, isopropanol, dioxane, acetonitrile and tetrahydrofuran.

8. The reaction method according to claim 6, wherein the internal olefin is selected from a group consisting of: 2-butene, cis-trans-2-pentene, cis-trans-2-hexene, cis-trans-3-hexene, cis-trans-2-heptene, cis-trans-3-heptene, cis-trans-2-octene, cis-trans-3-octene, cis-trans-4-octene, cis-trans-2-nonene, cis-trans-3-nonene, cis-trans-4-nonene, cis-trans-2-decene, cis-trans-3-decene, cis-trans-4-decene, and cis-trans-5-decene.

* * * * *

UNITED STATES PATENT AND TRADEMARK OFFICE
CERTIFICATE OF CORRECTION

PATENT NO. : 10,766,833 B2
APPLICATION NO. : 16/509530
DATED : September 8, 2020
INVENTOR(S) : Zhang et al.

Page 1 of 1

It is certified that error appears in the above-identified patent and that said Letters Patent is hereby corrected as shown below:

On the Title Page

"Item (12)" delete "Zhang" and insert --Zhang et al.--

"Item (72)" should be corrected to read:
Inventor 1: Runtong ZHANG SHENZHEN CHINA
Inventor 2: Xumu ZHANG SHENZHEN CHINA Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*